(12) United States Patent
Mekonnen et al.

(10) Patent No.: US 9,084,335 B2
(45) Date of Patent: Jul. 14, 2015

(54) HIGH FREQUENCY POWER DISTRIBUTION UNIT FOR A CT SYSTEM

(71) Applicant: General Electric Company, Schenectady, NY (US)

(72) Inventors: Ezana T. Mekonnen, Waukesha, WI (US); Jason Stuart Katcha, Waukesha, WI (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 101 days.

(21) Appl. No.: 14/036,324

(22) Filed: Sep. 25, 2013

(65) Prior Publication Data

US 2015/0085969 A1 Mar. 26, 2015

(51) Int. Cl.
  H05G 1/20 (2006.01)
  H05G 1/10 (2006.01)
  A61B 6/03 (2006.01)
  G01V 5/00 (2006.01)

(52) U.S. Cl.
  CPC ... *H05G 1/10* (2013.01); *A61B 6/032* (2013.01); *A61B 6/035* (2013.01); *G01V 5/005* (2013.01); *H05G 1/20* (2013.01)

(58) Field of Classification Search
  CPC ............ A61B 6/032; H05G 1/10; H05G 1/20
  See application file for complete search history.

(56) References Cited

U.S. PATENT DOCUMENTS

| 4,200,795 | A  | * | 4/1980  | Kawamura et al. | 378/106 |
| 5,808,376 | A  | * | 9/1998  | Gordon et al.   | 307/66  |
| 6,975,698 | B2 | * | 12/2005 | Katcha et al.   | 378/15  |
| 7,110,488 | B2 | * | 9/2006  | Katcha et al.   | 378/15  |
| 8,379,797 | B2 | * | 2/2013  | Abenaim et al.  | 378/103 |
| 2004/0264642 | A1 | * | 12/2004 | Katcha et al. | 378/107 |
| 2012/0027161 | A1 | * | 2/2012  | Abenaim et al. | 378/4  |

* cited by examiner

*Primary Examiner* — Michael Logie
(74) *Attorney, Agent, or Firm* — Lucas Divine; General Electric Company

(57) ABSTRACT

A CT system includes an x-ray source, a high-voltage power supply (HVPS) coupled to the x-ray source, and a high-frequency power distribution unit (HFPDU) having an input bus that is coupleable to a three-phase source, and having an output bus. The HFPDU includes a three-phase rectifier coupled to the input bus and configured to output a DC current to an inverter, the inverter configured to convert the DC current to an AC current, and output the AC current to a primary winding of an isolation transformer, and the isolation transformer having a secondary output to an isolation transformer, that is coupled to a full bridge rectifier, to produce DC current to the output bus and to DC bus loads of the CT system.

20 Claims, 5 Drawing Sheets

HIGH FREQUENCY POWER DISTRIBUTION UNIT FOR A CT SYSTEM

BACKGROUND

This disclosure relates generally to diagnostic imaging and, more particularly, to improved power distribution unit for a computed tomography (CT) system.

Typically, in computed tomography (CT) imaging systems, an x-ray source emits a fan or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are transmitted to the data processing system for image reconstruction. Imaging data may be obtained using x-rays that are generated at a single polychromatic energy. However, some systems may obtain multi-energy images that provide additional information for generating images.

The x-ray generator of a CT system is typically located within the gantry and, as such, rotates about an imaging bore during data acquisition on a rotatable side of the gantry. The x-ray generator includes the x-ray source, a high voltage power supply (HVPS), and an inverter that is operationally connected to a slip ring. External to the slip ring and on the stationary side of the gantry is a power distribution unit (PDU). The inverter is typically fed with a DC voltage, for example, 650 VDC, and generates an AC waveform of, for example, approximately 300 VAC, at a frequency of typically 20-50 kHz. The AC frequency is fed to the HV tank, which has a transformer and rectifiers that develop a DC HV potential. The HV potential is applied to the x-ray source.

According to one known configuration, a typical PDU used in an imaging application such as CT includes a large and relatively expensive transformer that operates at line frequency, such as 50 or 60 Hz. Multiple secondary windings generate unregulated DC voltage for X-ray generation, and generate AC power to the rest of the system. A large capacitor, between the PDU and the x-ray inverter, is used to minimize voltage droop, and as a result mechanical contactors are included to limit inrush current due to the large capacitor. The mechanical contactors can cause reliability problems over time. In addition, the large transformer typically remains energized even when the CT system is not in use, consuming in some known systems 500 W or more.

Therefore, it would be desirable to have an improved power distribution unit for a CT system.

BRIEF DESCRIPTION

Embodiments are directed toward a method and apparatus to an improved power distribution unit for a CT system.

According to one aspect, A CT system includes an x-ray source, a high-voltage power supply (HVPS) coupled to the x-ray source, and a high-frequency power distribution unit (HFPDU) having an input bus that is coupleable to a three-phase source, and having an output bus. The HFPDU includes a three-phase rectifier coupled to the input bus and configured to output a DC current to an inverter, the inverter configured to convert the DC current to an AC current, and output the AC current to a primary winding of an isolation transformer, and the isolation transformer having a secondary output to an isolation transformer, that is coupled to a full bridge rectifier, to produce DC current to the output bus and to DC bus loads of the CT system.

According to another aspect, a method of manufacturing a CT system includes attaching an x-ray source to a gantry, coupling a high-voltage tank to the x-ray source, and coupling a DC output of a high-frequency power distribution unit (HFPDU) to an input of the high-voltage power supply (HVPS). The HFPDU includes a three-phase rectifier coupled to an input bus of the HFPDU, the rectifier configured to output a DC current to an inverter, the inverter configured to convert the DC current to an AC current, and output the AC current to a primary winding of an isolation transformer, and the isolation transformer having a secondary output to the isolation transformer, that is coupled to a full bridge rectifier, to produce DC current to the output bus and to DC bus loads of the CT system.

According to yet another aspect, a high-frequency power distribution unit (HFPDU) for providing power for a CT system, the HFPDU having an input bus that is coupleable to a three-phase source, and having an output bus, the HFPDU including a three-phase rectifier coupled to the input bus and configured to output a DC current to an inverter, the inverter configured to convert the DC current to an AC current, and output the AC current to a primary winding of an isolation transformer, and the isolation transformer having a secondary output to an isolation transformer, that is coupled to a full bridge rectifier, to produce DC current to the output bus and to DC bus loads of a CT system.

Various other features and advantages will be made apparent from the following detailed description and the drawings.

DETAILED DESCRIPTION

The operating environment of disclosed embodiments is described with respect to a sixty-four-slice computed tomography (CT) system. However, it will be appreciated by those skilled in the art that embodiments are equally applicable for use with other multi-slice configurations. Moreover, disclosed embodiments will be described with respect to the detection and conversion of x-rays. However, one skilled in the art will further appreciate that embodiments are equally applicable for the detection and conversion of other high frequency electromagnetic energy. Disclosed embodiments will be described with respect to a "third generation" CT scanner, but is equally applicable with other CT systems as well as vascular and surgical C-arm systems and other x-ray tomography systems.

Figure 1:
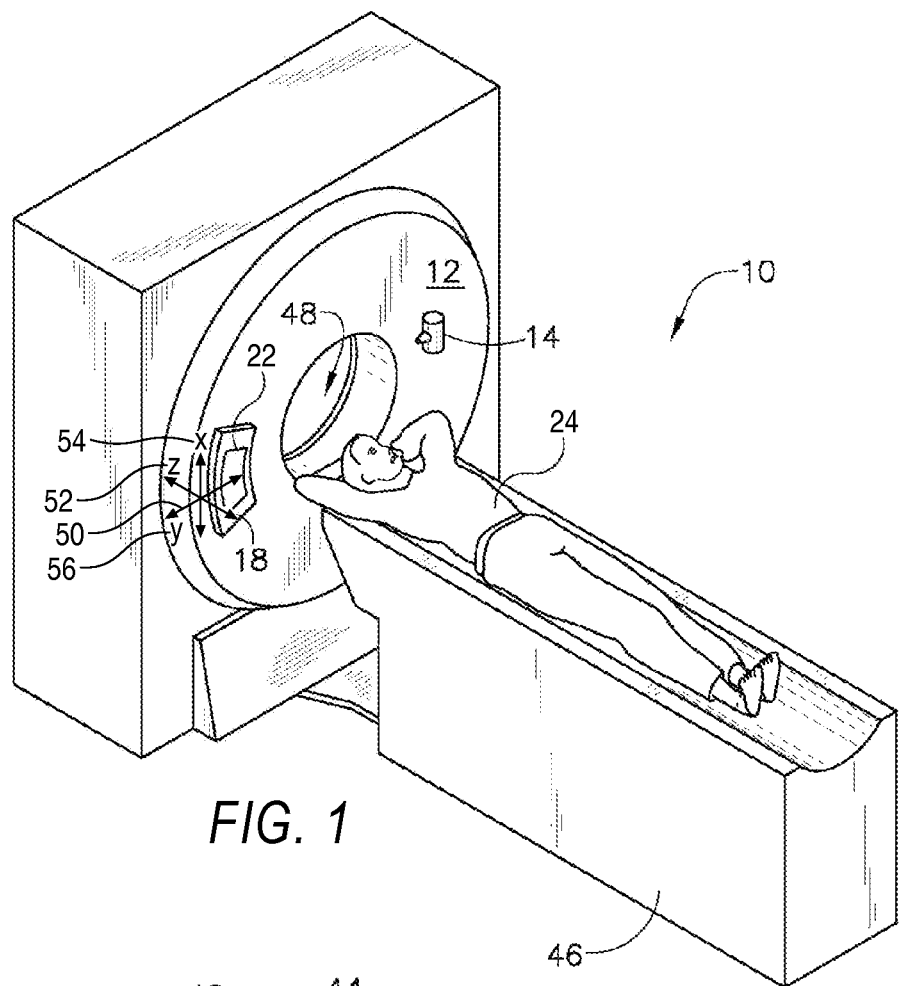
FIG. 1 is a pictorial view of a CT imaging system that incorporates disclosed embodiments.
Figure 2:
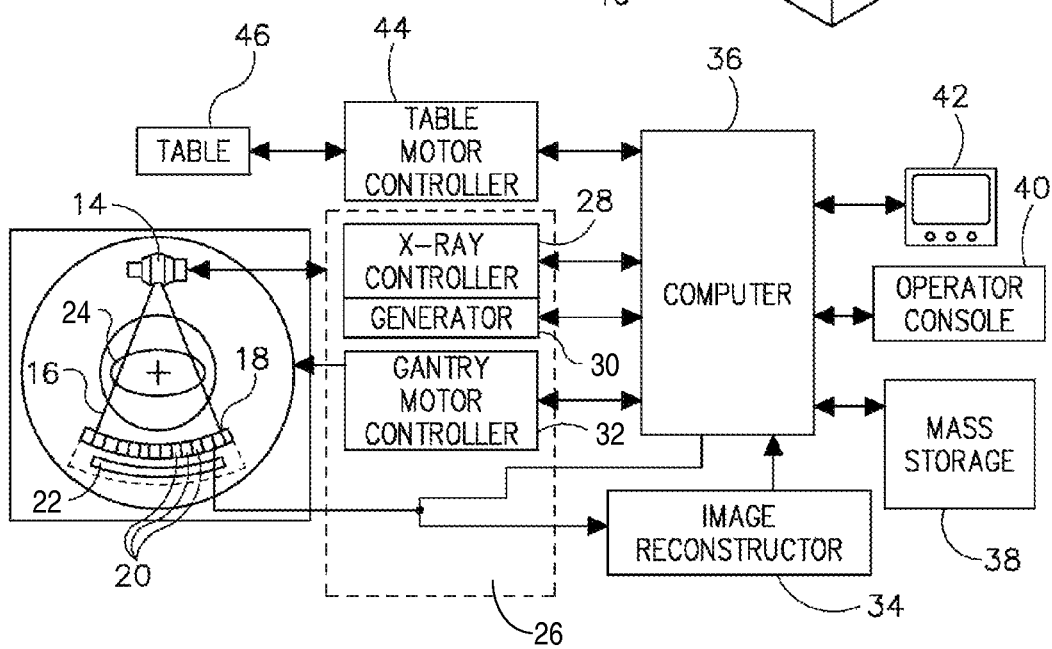
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. X-ray source 14 includes either a stationary target or a rotating target. Detector assembly 18 is formed by a plurality of detectors 20 data acquisition systems (DAS) 22. The plurality of detectors 20 sense the projected x-rays that pass through a medical patient 24, and DAS 22 converts the data to digital signals for subsequent processing. Each detector 20 produces an analog electrical signal that represents the intensity of an impinging x-ray beam and hence the attenuated beam as it passes through patient 24. During a scan to acquire x-ray projection data, gantry 12 and the components mounted thereon rotate about a center of rotation.

Rotation of gantry 12 and the operation of x-ray source 14 are governed by a control mechanism 26 of CT system 10. Control mechanism 26 includes an x-ray controller 28 and generator 30 that provides power and timing signals to x-ray source 14 and a gantry motor controller 32 that controls the rotational speed and position of gantry 12. An image reconstructor 34 receives sampled and digitized x-ray data from DAS 22 and performs high speed image reconstruction. The reconstructed image is applied as an input to a computer 36 which stores the image in a mass storage device 38.

Computer 36 also receives commands and scanning parameters from an operator via an operator console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 22, x-ray controller 28, and gantry motor controller 32. In addition, computer 36 operates a table motor controller 44 which controls a motorized table 46 to position patient 24 and gantry 12. Particularly, table 46 moves patients 24 through a gantry opening 48 in whole or in part. A coordinate system 50 for detector assembly 18 defines a patient or Z-axis 52 along which patient 24 is moved in and out of opening 48, a gantry circumferential or X-axis 54 along which detector assembly 18 passes, and a Y-axis 56 that passes along a direction from a focal spot of X-ray source 14 to detector assembly 18.

X-ray source 14, in accordance with present embodiments, is configured to emit x-rays or x-ray beam 16 at one or more energies. For example, x-ray source 14 may be configured to switch between relatively low energy polychromatic emission spectra (e.g., at approximately 80 kVp) and relatively high energy polychromatic emission spectra (e.g., at approximately 140 kVp). As will be appreciated, x-ray source 14 may also be operated so as to emit x-rays at more than two different energies. Similarly, x-ray source 14 may emit at polychromatic spectra localized around energy levels (i.e., kVp ranges) other than those listed herein (e.g., 100 kVP, 120 kVP, etc.). Selection of the respective energy levels for emission may be based, at least in part, on the anatomy being imaged.

In some embodiments X-ray controller 28 may be configured to selectively activate x-ray source 14 such that tubes or emitters at different locations within system 10 may be operated in synchrony with one another or independent of one another. In certain embodiments discussed herein, the x-ray controller 28 may be configured to provide fast-kVp switching of x-ray source 14 so as to rapidly switch source 14 to emit X-rays at the respective polychromatic energy spectra in succession during an image acquisition session. For example, in a dual-energy imaging context, x-ray controller 28 may operate x-ray source 14 so that x-ray source 14 alternately emits x-rays at the two polychromatic energy spectra of interest, such that adjacent projections are acquired at different energies (i.e., a first projection is acquired at high energy, the second projection is acquired at low energy, the third projection is acquired at high energy, and so forth). In one such implementation, fast-kVp switching operation performed by x-ray controller 28 yields temporally registered projection data. In some embodiments, other modes of data acquisition and processing may be utilized. For example, a low pitch helical mode, rotate-rotate axial mode, N×M mode (e.g., N low-kVp views and M high-kVP views) may be utilized to acquire dual-energy datasets.

Figure 3:
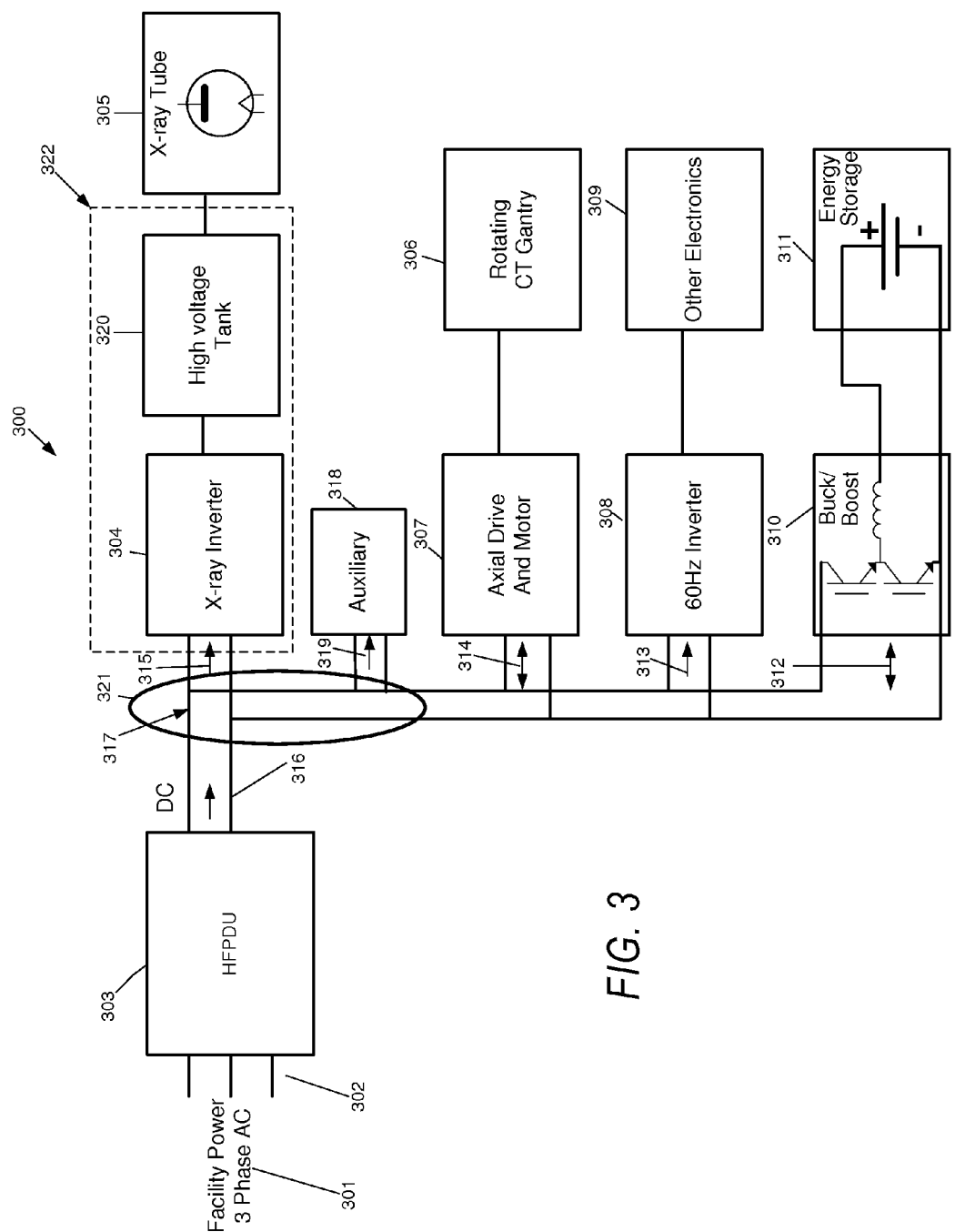
FIG. 3 is a schematic of an HVPS, X-ray source, axial drive and other 60 Hz loads for a CT imaging system such as illustrated in FIGS. 1 and 2.

Referring to FIG. 3, an imaging system electrical circuit 300 is illustrated that is incorporated into system 10 shown in FIGS. 1 and 2. Circuit 300 includes a DC or electrical bus 317 coupled to a DC output 316 of a high-frequency power distribution unit (HFPDU) 303. An axial drive and gantry motor 307 is electrically coupled to the electrical bus 317. An AC input 302 to the HFPDU 303 is coupleable to a 3-phase AC electrical source 301. A gantry 306 (similar to gantry 12 of FIGS. 1 and 2) is mechanically coupled to gantry motor 307 (similar to gantry motor controller 32 of FIG. 2), and rotational energy in rotating gantry is regeneratively converted to DC electrical energy in gantry motor 307 during gantry braking, and the DC electrical energy is provided to the electrical bus 317.

Circuit 300 includes a high voltage power supply (HVPS) 322 (similar to generator 30 of FIG. 2) that includes inverter 304 and high voltage tank 320, and HVPS 322 is coupled to electrical bus 317. HVPS 322 is configured to provide power to an x-ray tube 305 (similar to x-ray tube 14 of FIGS. 1 and 2). Circuit 300 includes one or more components 309 coupled to electrical bus 317, the one or more components 309 including, as examples and consistent with FIGS. 1 and 2, a data acquisition system (DAQ) 22, a detector cooling fan 23, and a system control computer 36. The one or more components 309 are powered by the 60 Hz DC to AC Converter 308.

External to rotating base (not shown) and electrically connected to a slip ring 321 is the HFPDU 303 that is stationary and therefore does not rotate with x-ray tube 305, tank 320, and inverter 304. Inverter 304 is provided 315 with a DC voltage, for example, 650 VDC, which generates an AC voltage waveform, for example, approximately 300 VAC, at a specified frequency, e.g. 20 kHz-50 kHz. The AC voltage is then fed to the HV tank 320, which has a transformer and rectifiers (not shown) that develops a DC HV potential. The HV potential is then applied to the x-ray tube 305. Rotating base (not shown) is also designed with one or more auxiliary devices 318 that may include auxiliary power devices with DC power 319. As such, X-ray inverter 304, HV tank 320, and X-ray tube 305 are positioned on the rotating side of slip ring 321. As such, a relatively low DC voltage is supplied to slip ring 321 which is then transferred to X-ray inverter 304 for conditioning. FIG. 3 illustrates one exemplary embodiment in which inverter 304 is positioned on rotating base (not shown). However, in another example (not shown), inverter 304 is external to slip ring 321 and on a stationary side of the gantry.

In an optional embodiment, circuit 300 includes an energy storage device 311 coupled to bus 317, and in one example energy storage device 311 is a lithium ion battery having a higher energy density and peak power capability than conventional batteries. Further, energy storage device 311 is coupled via a voltage stepping device to a buck-boost converter 310 that is coupled between the energy storage device 311 and bus 317. Typically, a buck-boost converter such as converter 310 operates as a DC stepper to step up the DC voltage in one direction and step down the voltage in the other direction. In this case, DC bus 317 includes a voltage sufficient to power the inverter 304, gantry motor 307, and other electrical components 309. Buck-boost converter may therefore be appropriately used to step up and down, accordingly, per the voltage on bus 317 and per the operating voltage of energy storage 311.

In one embodiment, however, circuit 300 does not include an energy storage unit, such as energy storage 311 (or converter 310) coupled to bus 317. Thus, in the embodiment without energy storage 311, system design and operation is simpler and is a less expensive alternative. However, because no energy is stored, then the regenerative energy from the rotating gantry is concurrently used, or is dissipated and lost. Thus, whether circuit 300 includes optional energy storage 311 may depend on a cost tradeoff for the additional functionality of energy storage and additional system complexity, versus the ability to recover cost to extent as lost energy. Further, energy storage 311 can further provide additional power to the system during interruptions in power supply, thus serving as an uninterruptible power supply (UPS).

In operation, 3-phase AC facility power is provided from source 301, and in one embodiment is 480 VAC at 150 KW. The power is converted to DC power in HFPDU 303 and passed as DC output 316 as DC electrical power. DC electrical power is thereby provided to bus 317, through which the power may be distributed the various system components as described. DC power may pass 315 to inverter 304, or may pass 313 to other system electronics 309. DC power may also pass 314, 312 to gantry motor 307 and energy storage 311, respectively, but as illustrated 314, 312 power may pass in both directions based on the mode of operation. That is, when powering gantry motor 307, power may pass to motor 307 from bus 317, but when operating in regenerative mode power may pass from motor 307 to bus 317. Similarly, power may pass 312 from bus 317 to storage 311, or power may pass from storage 311 to bus 317. In either case, when power is passing from gantry 306 and/or storage 311, then energy is passed to inverter 304, other system electronics 313, or auxiliary components 318.

As such, HFPDU 303 is coupled to DC bus 316 that includes the entire DC bus loads for the CT system, that include typically DC bus passing 315 to x-ray inverter 304, passing 319 to auxiliary loads 318, passing 314 to and from axial drive and motor 307, passing 313 to inverter 308, and passing to and from 312 buck-boost converter 310. In other words, circuit 300 includes bus 316, which is a DC bus and which provides DC power to the entire components of the CT system, according to the disclosure.

Figure 4:
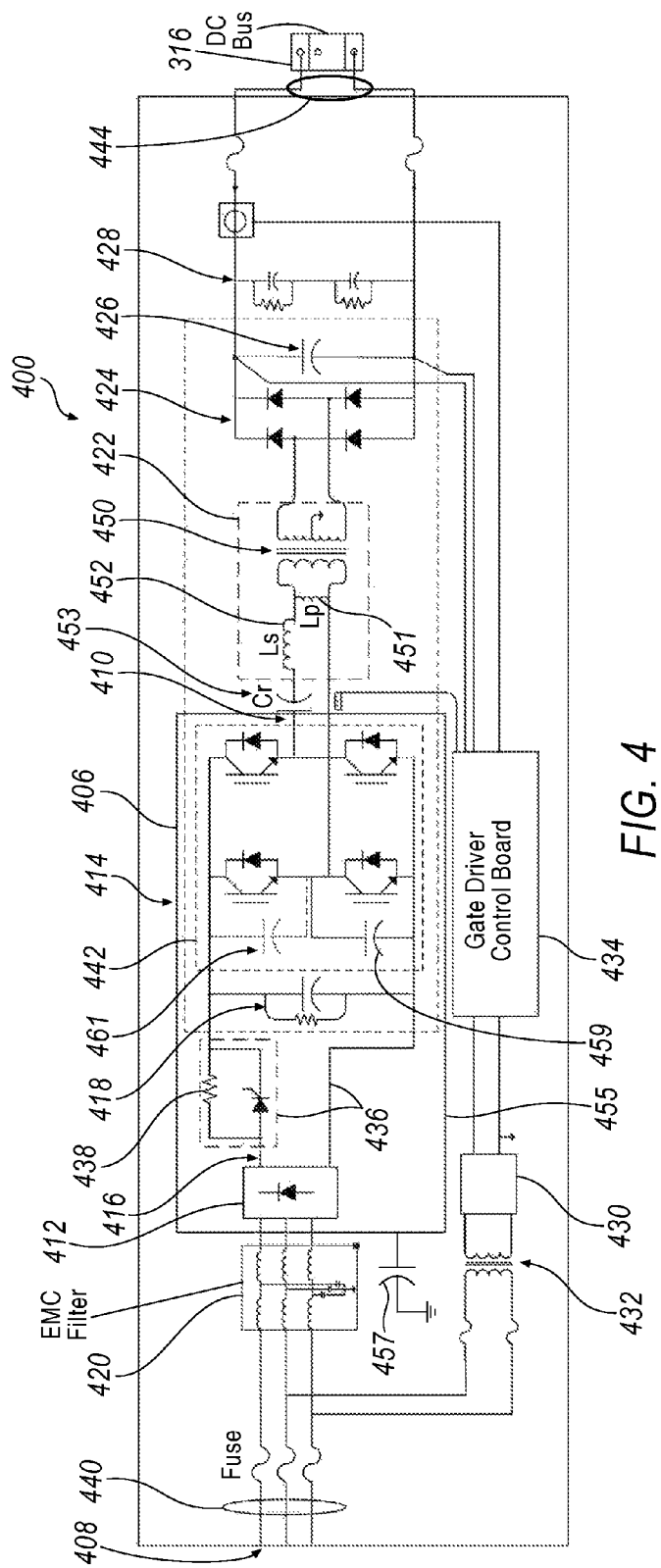
FIG. 4 illustrates a high-frequency power distribution unit (HFPDU) 400 for a CT system, such as system 10 of FIGS. 1 and 2.

Referring to FIG. 4, a high-frequency power distribution unit (HFPDU) 400, such as HFPDU 303 of FIG. 3, is disclosed. HFPDU 400 is shown with connection to a DC bus, which corresponds with DC bus 317 of FIG. 3. HFPDU 400 includes a high frequency transformer 422 coupled to full bridge rectifier 424, and a front-end circuit 406 having an input bus 408. Rectifier 424 includes a capacitor 426, and capacitors 428. Input bus 408 is coupleable to a three-phase source, which in one embodiment is a 480 V, 3-phase source supply from a utility. Front-end circuit 406 includes an output bus 410 coupled to high frequency transformer 422 to output an AC current thereto. Front-end circuit 406 includes a three-phase rectifier 412 coupled to input bus 408, and three-phase rectifier 412 is configured to output a DC current to an inverter 414, from a rectifier output bus 416, as will be further discussed.

Inverter 414 is coupled to output bus 410, and inverter 414 is configured to convert the DC current to the AC current. Front-end circuit 406 includes a bus capacitor 418 and a noise filter 420 for each of the lines from input bus 408. The resonance circuit 422 includes an isolation transformer 450, series inductance 452 integrated into the design of isolation transformer 450, series capacitor 453, and parallel inductor 451. In one embodiment, series inductance 452, and parallel inductor 451 are part of the isolation transformer 450 leakage and magnetizing inductance respectively. In one embodiment, isolation transformer 450 includes a gap in a ferrite core that creates a magnetizing inductance. Isolation transformer 450 may also include spacers for leakage inductance, separating the primary from the secondary and causing additional leakage inductance. Thus a resonant inductance is achieved, reducing the amount of losses in the inverter 414 switches. That is, the isolation transformer 450 incorporates leakage inductance and magnetizing inductance that will be used as series resonance inductance and parallel resonance inductance respectively in the resonance circuitry. HFPDU 400 includes a power supply 430 that is coupled via a secondary transformer 432 to two of the lines of input bus 408, and which provides power to a gate driver/control board 434, for operating elements of an H-bridge 442. Front-end circuit 406 also includes a silicon-controlled rectifier (SCR) 436 and a resistor 438 in parallel with SCR 436 to serve as "soft start" function.

Three-phase rectifiers, such as three-phase rectifier 412, changes AC to DC and includes a generally DC output with minimal peak-to-peak ripple, hereinafter referred to as a DC output or current. In one disclosed embodiment, three-phase rectifier 412 uses diodes (FIG. 5), and in another embodiment, three-phase rectifier 412 uses thyristors.

Figure 5:
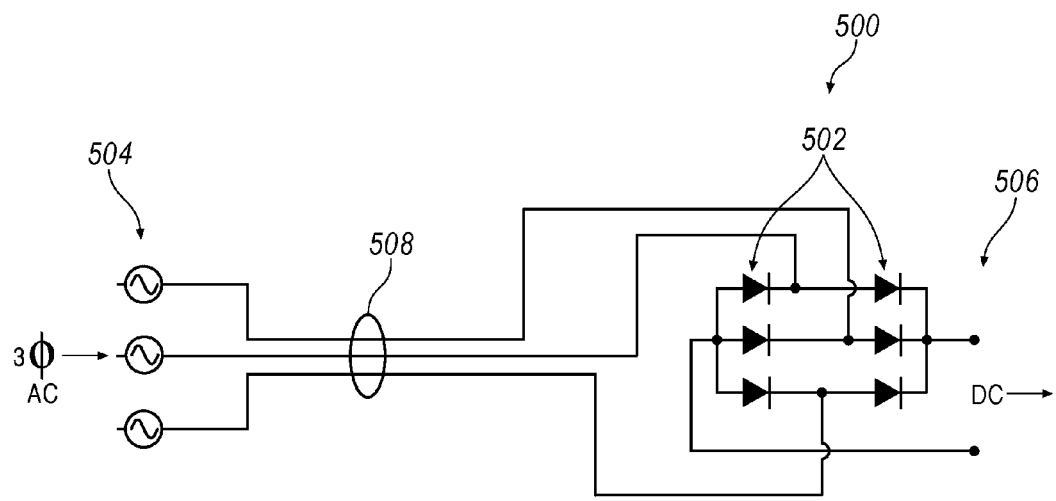
FIG. 5 illustrates a three-phase rectifier using diodes, according to one embodiment.

Referring to FIG. 5, a rectifier 500, corresponding to rectifier 412 of FIG. 4, includes diodes 502 configured in a bridge arrangement and coupled to an input bus 504 and an output bus 506. As commonly known, a diode is generally a passive electrical device exhibiting non-linear characteristics, having low resistance to current flow in one direction, and high resistance to current flow in the opposite direction. Voltage drop in the 'forward' current direction is nominal and may be, in examples, between 0.5 and 0.8 V, while having nearly zero current in the 'reverse' current direction until a breakdown occurs above a breakdown voltage, as is commonly known.

As shown, diodes 502 are arranged in a bridge configuration to convert a three-phase current from the input bus to the DC current. Rectifier 500 is positioned within front-end circuit 406 such that three-phase power is conveyed along lines 508, which correspond with lines 440 of FIG. 4. Three-phase current passes along each of lines 508 and, due to the arrangement of diodes 502, a composite or final DC current results and is subsequently passed to inverter 414. In another embodiment, (not shown), a rectifier corresponding to rectifier 412 of FIG. 4, includes thyristors configured in an alternate bridge arrangement and coupled to an input bus and an output bus.

Referring back to FIG. 4, HFPDU 400 includes the inverter 414 that includes, in the illustrated arrangement, the full-bridge or "H" configuration of four (4) power switches 442 that switch in a pattern to control the inverter current, and thus output power of inverter 414. The full-bridge includes two legs, each of which includes an upper and a lower switch. The switches are typically insulated-gate bipolar transistors or IGBTs. In this known configuration of four power switches, switching in the two legs is controlled in a pattern by a controller (not shown) such that either the upper or lower switch of each leg is on. The switching between on and off is controlled in such a fashion that a high-frequency inverter current is formed, which is in turn fed to the high frequency transformer for isolation before being rectified back to produce regulated DC bus. One known switching frequency of a four-switch design is 50 kHz. In such fashion, the controller is coupled to the switches and configured to operate the switches to regulate the output DC bus. It is further contemplated, in one embodiment, that a "snubber capacitor" 459 is included at the input to power switches 442 as shown, and in an alternative location 461, which smooths the switching events in inverter 414.

In one embodiment (not shown), inverter 414 includes at least one additional leg of switches having respective upper switches and lower switches. The at least one additional leg of switches includes a second H-bridge configuration of switches that includes a third leg and/or a fourth leg. The third and fourth legs include respective upper and lower switches, and thus also include additional switches. The additional third leg and/or fourth leg can be interleaved in operation along with their corresponding switches, according to another embodiment.

As stated, front-end circuit 406 includes SCR 436 that is electrically coupled between the three-phase rectifier circuit and the inverter. SCR 436, as is commonly known, is a multi-layer solid state current controlling device. In some embodiments, an SCR is considered to be synonymous with a thyristor. SCRs are unidirectional devices that conduct current in only one direction, and can be triggered by current in a gate. Operation of SCR 436 is controlled by a controller and functions, in the embodiment illustrated, in parallel with resistor 438. Thus, in operation, a "soft start" of the system occurs when SCR 436 is off and charging of the system occurs through resistor 438. SCR 436 is then turned on and current thereafter passes essentially unimpeded through SCR 436 during system operation.

According to one embodiment, front-end circuit 406 is positioned on a heat sink 455, that is electrically isolated or a "floating heat sink", to reduce the possibility of ground fault due to being line connected. If not isolated or floating, a failure mode that could arise is a voltage punch-through to the substrate, leading to a ground fault, The use of a floating heat sink thus not only isolates the fault from passing to ground and triggering a Ground Fault Interrupter (GFI), but also limits the parasitic coupling path for EMC noise. In one embodiment, heat sink 455 includes a capacitor 457 to ground to further reduce the possibility of triggering a GFI. As can be appreciated, however, ground faults occurring.

Typically, capacitor 426 is on the order of 10000 micro-Farads, but due to the disclosed combination of inverter 414 that is coupled to high frequency transformer 422, it is contemplated that a much smaller capacitor 426, such as 2000 micro-Farads, is adequate in the disclosed circuit. Also, capacitor 418 is typically of order 1000 micro-Farads, but due to the disclosed combination of inverter 414 that is coupled to high frequency transformer 422, it is contemplated that a much smaller capacitor 418, such as 500 micro-Farads, is adequate in the disclosed circuit.

A method of manufacturing a CT system is disclosed that includes coupling x-ray inverter 304 to an output 444 of HFPDU 400. The method includes coupling front-end circuit 406 to resonance circuitry 422, though inverter 414 outputs an AC current thereto, and rectifier 424 coupled to the output bus configured to output a DC current.

As such, an active front-end is disclosed that uses a small capacitance, yet supports a wide variety of input voltages and frequencies. In the HFPDU 400, the switching devices will be used to modulate the power flow while creating high frequency AC voltage that is used together with a high frequency transformer, such as transformer 422, thus providing galvanic isolation. The increase in the AC frequency from the switching devices of the HFPDU results in a significant reduction in the size of the isolation transformer 422. The method employs a high efficiency power resonant converter such as "series-resonance converter" as a means of power converter, which allows the input voltage to vary, in one example, up to +/−30%, while maintaining +/−5% regulation on the output.

The HFPDU 400 is an overhaul of a more typical power architecture approach of using a bulky and expensive transformer (not shown) that operates at the line frequency. Some of the clinically relevant features of CT systems include faster rotation, larger bore size, more robust ultra-fast KV switching, and higher x-ray tube power, as examples. Among other things, the aforementioned features thereby tend toward higher power for x-ray generation, and tighter output voltage regulation to the PDU to support faster speed and optimize KV waveform fidelity. The disclosed embodiments provide galvanic isolation, and regulate the output power with only a fifth of the original footprint, in one example, which is the result of higher operating frequency of the transformer resulting in significant reduction of material need for a transformer.

The disclosed embodiments actively regulate power flow of the CT system, and allow wider input voltage variation, while maintaining tighter output voltage regulation. In addition, the HFDPU 400 architecture creates an effective isolation of grid side disturbance from getting in to the load. This may be especially beneficial in a site where power quality may be sub-standard, and such incidence on the power line might either cause scan abort or damage to equipment. Current mitigation for such risk is to include a full or partial uninterruptible power supply (UPS) to improve power quality. Also one of the challenges of such architecture is the possibility of ground fault due to being line connected, and the disclosed embodiments address that concern though the use of an electrically isolated or "floating heat sink". The use of a floating heat sink not only isolate fault from making to ground and triggering a ground fault interrupter (GFI), but also limits parasitic coupling path for EMC noise.

The HFPDU 400 incorporates intelligence for active monitoring of power. It is not only capable of providing power usage but also provides a significant amount of power saving during sleep mode (which can be as high as 500 W in a traditional system, but may be as little as 10 W as a result of implementation of the disclosed embodiments). This thereby enables a more energy efficient CT system, and is found to be important in some States in the US that provide reimbursement for such capability. The use of active electronic to control the output voltage reduces the need for large capacitance that are typically included to limit voltage droop during x-ray exposure by controlling the voltage. In addition, the regulated output voltage also reduces the current rating of the motor driver system, resulting in a lower cost motor driver and improvement in the thermal performance (i.e. reliability of x-ray generator). The HFPDU also provides inherent brown-out ride-thru and extreme power quality.

Figure 6:
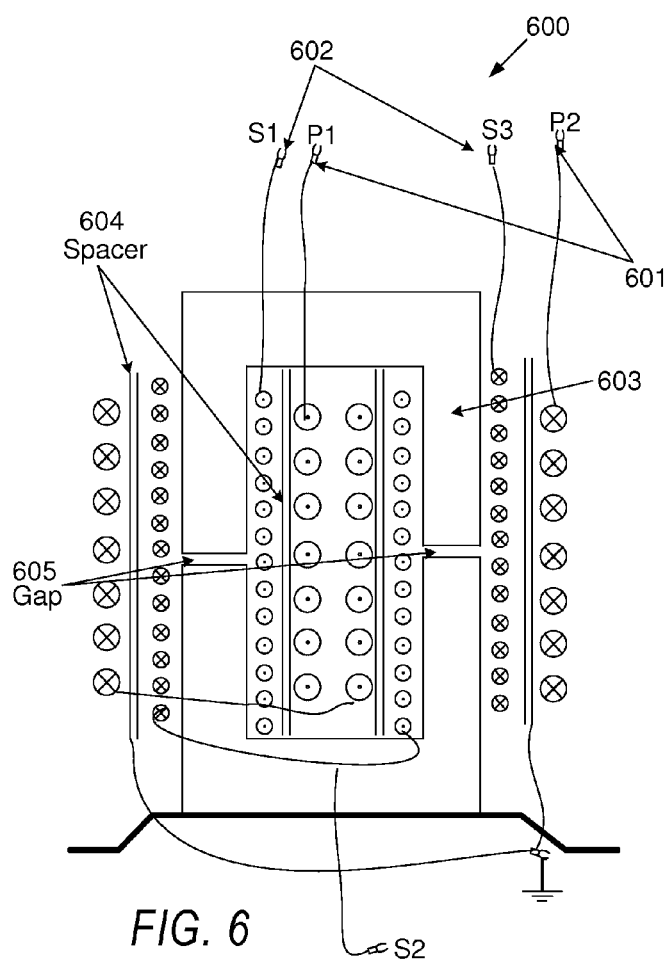
FIG. 6 illustrates an isolation transformer.

FIG. 6 illustrates cross section view of a transformer 600, also referred to as transformer 422 of FIG. 4. A primary side or winding 601 of the transformer 600 is shown capacitively coupled to inverter 414 output bus 410 though series capacitor 453. A secondary side or winding 602 of the transformer 600 is shown with connection to rectifier 424 to produce DC current. The transformer 600 also includes a gap 605 within in a core 603 to create a lower magnetizing inductance 451 of FIG. 4. A typical value of magnetizing inductance can be 100 uH. Isolation transformer 600 also includes a spacer material 604, between the primary winding 601 and the secondary winding 602 to produce leakage inductance that is used as series inductance 452 of FIG. 4.

Figure 7:
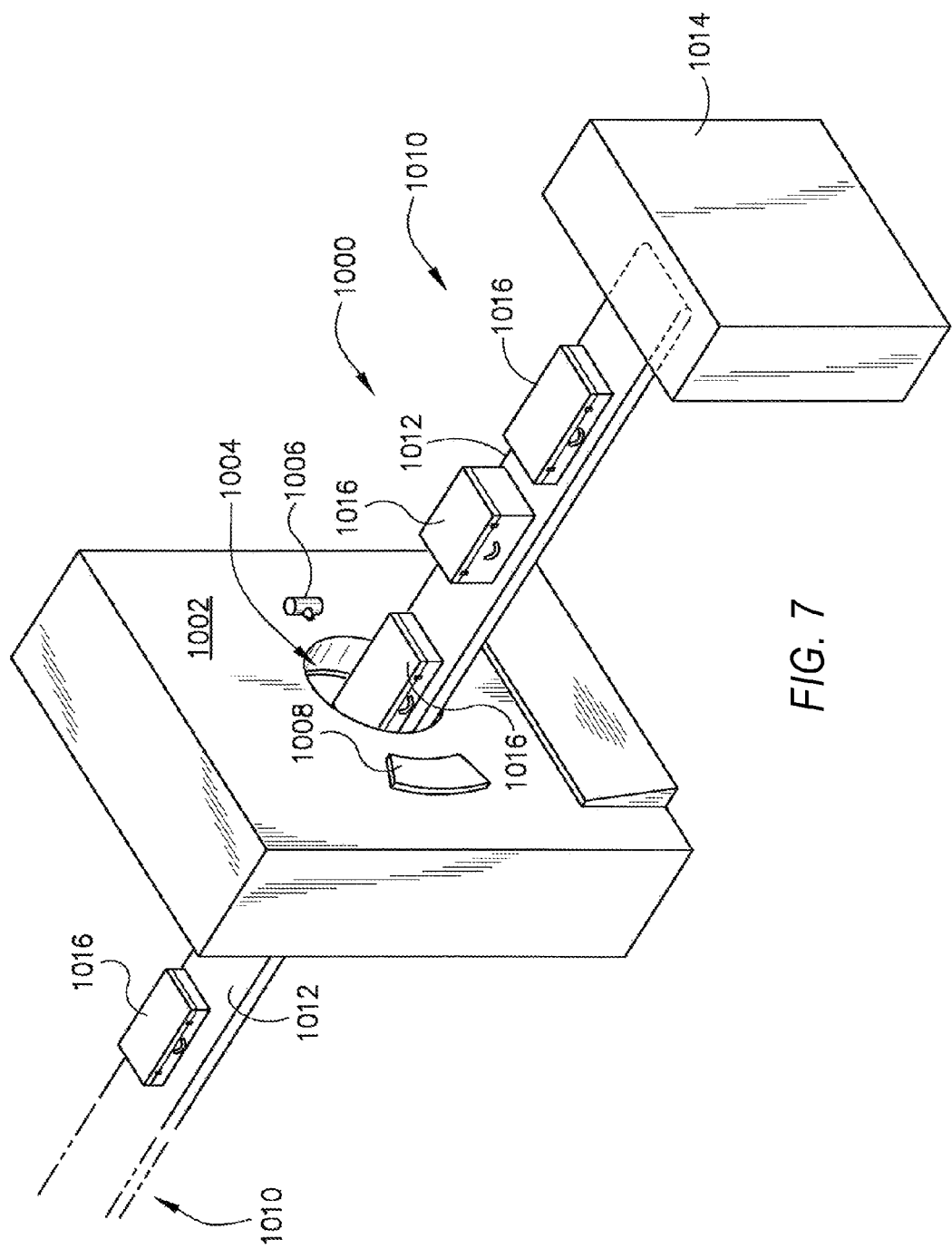
FIG. 7 is a pictorial view of a CT system for use with a non-invasive package inspection system according to an embodiment.

Referring now to FIG. 7, there is shown a package/baggage inspection system 1000 that can use the image acquisition and reconstructions techniques according to embodiments disclosed and which includes a rotatable gantry 1002 having an opening 1004 therein through which packages or pieces of baggage may pass. The rotatable gantry 1002 houses one or more x-ray energy sources 1006 as well as a detector assembly 1008 having scintillator arrays comprised of scintillator cells. A conveyor system 1010 is also provided and includes a conveyor belt 1012 supported by structure 1014 to automatically and continuously pass packages or baggage pieces 1016 through opening 1004 to be scanned. Objects 1016 are passed through opening 1004 by conveyor belt 1012, imaging data is then acquired, and the conveyor belt 1012 removes the packages 1016 from opening 1004 in a controlled and continuous manner. As a result, postal inspectors, baggage handlers, and other security personnel may non-invasively inspect the contents of packages 1016 for explosives, knives, guns, contraband, etc.

An implementation of system 10 and/or 1000 in an example comprises a plurality of components such as one or more of electronic components, hardware components, and/or computer software components. A number of such components can be combined or divided in an implementation of the system 10 and/or 1000. An exemplary component of an implementation of the system 10 and/or 1000 employs and/or comprises a set and/or series of computer instructions written in or implemented with any of a number of programming languages, as will be appreciated by those skilled in the art. An implementation of system 10 and/or 1000 in an example comprises any (e.g., horizontal, oblique, or vertical) orientation, with the description and figures herein illustrating an exemplary orientation of an implementation of the system 10 and/or 1000, for explanatory purposes.

An implementation of system 10 and/or system 1000 in an example employs one or more computer readable signal bearing media. A computer-readable signal-bearing medium in an example stores software, firmware and/or assembly language for performing one or more portions of one or more implementations. An example of a computer-readable signal-bearing medium for an implementation of the system 10 and/or the system 1000 comprises the recordable data storage medium of the image reconstructor 34, and/or mass storage device 38 of computer 36. A computer-readable signal-bearing medium for an implementation of the system 10 and/or the system 1000 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 1000, for instance, one or more of a telephone network, a local area network ("LAN"), a wide area network ("WAN"), the Internet, and/or a wireless network.

According to one embodiment, a CT system includes an x-ray source, a high-voltage power supply (HVPS) coupled to the x-ray source, and a high-frequency power distribution unit (HFPDU) having an input bus that is coupleable to a three-phase source, and having an output bus. The HFPDU includes a three-phase rectifier coupled to the input bus and configured to output a DC current to an inverter, the inverter configured to convert the DC current to an AC current, and output the AC current to a primary winding of an isolation transformer, and the isolation transformer having a secondary output to an isolation transformer, that is coupled to a full bridge rectifier, to produce DC current to the output bus and to DC bus loads of the CT system.

According to another embodiment, a method of manufacturing a CT system includes attaching an x-ray source to a gantry, coupling a high-voltage tank to the x-ray source, and coupling a DC output of a high-frequency power distribution unit (HFPDU) to an input of the high-voltage tank. The HFPDU includes a three-phase rectifier coupled to an input bus of the HFPDU, the rectifier configured to output a DC current to an inverter, the inverter configured to convert the DC current to an AC current, and output the AC current to a primary winding of an isolation transformer, and the isolation transformer having a secondary output to the isolation transformer, that is coupled to a full bridge rectifier, to produce DC current to the output bus and to DC bus loads of the CT system.

According to yet another embodiment, a high-frequency power distribution unit (HFPDU) for providing power for a CT system, the HFPDU having an input bus that is coupleable to a three-phase source, and having an output bus, the HFPDU including a three-phase rectifier coupled to the input bus and configured to output a DC current to an inverter, the inverter configured to convert the DC current to an AC current, and output the AC current to a primary winding of an isolation transformer, and the isolation transformer having a secondary output to an isolation transformer, that is coupled to a full bridge rectifier, to produce DC current to the output bus and to DC bus loads of a CT system.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

While the disclosed subject matter has been described in detail in connection with only a limited number of embodiments, it should be readily understood that the disclosure is not limited to such disclosed embodiments. Rather, that disclosed can be modified to incorporate any number of variations, alterations, substitutions or equivalent arrangements not heretofore described, but which are commensurate with the spirit and scope of the disclosure. Furthermore, while single energy and dual-energy techniques are discussed above, that disclosed encompasses approaches with more than two energies. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A CT system comprising:
an x-ray source;
a plurality of DC bus loads;
a high-voltage power supply (HVPS) coupled to the x-ray source; and
a high-frequency power distribution unit (HFPDU) having an input bus that is coupleable to a three-phase source, and having an output bus, the HFPDU comprising:
a three-phase rectifier coupled to the input bus and configured to output a DC current to an inverter;
the inverter configured to convert the DC current to an AC current, and output the AC current to a primary winding of an isolation transformer; and
the isolation transformer coupled to a full bridge rectifier, to produce DC current to the output bus and to DC bus loads of the CT system.

2. The CT system of claim 1, wherein the three-phase rectifier comprises a plurality of diodes arranged to convert a three-phase current from the input bus to the DC current.

3. The CT system of claim 1, wherein the HFPDU includes a series resonance converter, which includes the isolation transformer, to regulate the output DC bus voltage to the DC bus loads of the system.

4. The CT system of claim 3, wherein the series resonance converter comprises:
a ferrite core in the isolation transformer having a gap.

5. The CT system of claim 3, wherein the isolation transformer incorporates leakage inductance and magnetizing inductance that will be used as series resonance inductance and parallel resonance inductance respectively in the resonance circuitry.

6. The CT system of claim 1, wherein:
the inverter comprises an H-bridge configuration of switches; and
the CT system further comprises a controller coupled to the switches and configured to operate the switches to convert the DC current to the AC current.

7. The CT system of claim 1, wherein the DC bus loads include at least one of auxiliary device for the CT system, a gantry motor, an AC converter, and an energy storage device.

8. The CT system of claim 1, further comprising a heat sink, wherein the three-phase rectifier and the inverter are positioned on the heat sink, and the heat sink is electrically isolated from ground.

9. The CT system of claim 8, further comprising a capacitor positioned between the heat sink and ground.

10. The CT system of claim 1, wherein the inverter includes a snubber capacitor across a power switch thereof.

11. A method of manufacturing a CT system, comprising:
attaching an x-ray source to a gantry;
attaching a plurality of DC bus loads to a gantry;
coupling a high-voltage power supply (HVPS) to the x-ray source; and
coupling a DC output of a high-frequency power distribution unit (HFPDU) to an input of the high-voltage power supply (HVPS), the HFPDU comprising:
a three-phase rectifier coupled to an input bus of the HFPDU, the rectifier configured to output a DC current to an inverter;
the inverter configured to convert the DC current to an AC current, and output the AC current to a primary winding of an isolation transformer; and
the isolation transformer coupled to a full bridge rectifier, to produce DC current to the output bus and to DC bus loads of the CT system.

12. The method of claim 11, wherein the HFPDU includes a series resonance converter, which includes the isolation transformer, to regulate output DC bus voltage to the DC bus loads of the system.

13. The method of claim 12, wherein the series resonance converter comprises:
a ferrite core in the isolation transformer having a gap.

14. The method of claim 12, wherein the isolation transformer incorporates leakage inductance and magnetizing inductance that will be used as series resonance inductance and parallel resonance inductance respectively in the resonance circuitry.

15. The method of claim 11, wherein the DC bus loads include at least one of auxiliary device for the CT system, a gantry motor, an AC converter, and an energy storage device.

16. The method of claim 11, further comprising attaching the three-phase rectifier and the inverter to a heat sink that is electrically isolated from ground; and
connecting a capacitor to the heat sink and to ground.

17. A high-frequency power distribution unit (HFPDU) for providing power for a CT system, the HFPDU having an input bus that is coupleable to a three-phase source, and having an output bus connected to a plurality of DC bus loads, the HFPDU comprising:
a three-phase rectifier coupled to the input bus and configured to output a DC current to an inverter;
the inverter configured to convert the DC current to an AC current, and output the AC current to a primary winding of an isolation transformer; and
the isolation transformer coupled to a full bridge rectifier, to produce DC current to the output bus and to DC bus loads of the CT system.

18. The HFPDU of claim 17, wherein the HFPDU includes a series resonance converter, which includes the isolation transformer, to regulate the output DC bus voltage to the DC bus of the CT system, wherein the series resonance converter comprises:
A ferrite core in the isolation transformer having a gap.

19. The HFPDU of claim 17, wherein the DC bus loads include at least one of auxiliary device for the CT system, a gantry motor, an AC converter, and an energy storage device.

20. The HFPDU of claim 17, further comprising a heat sink, wherein the three-phase rectifier and the inverter are positioned on the heat sink, and the heat sink is electrically isolated from ground, and the capacitor positioned between the heat sink and ground.

* * * * *